United States Patent
Ferguson et al.

(10) Patent No.: US 9,655,612 B2
(45) Date of Patent: May 23, 2017

(54) SUTURE TAPE ASSEMBLY HAVING A MIDPOINT MARK

(71) Applicant: Riverpoint Medical, LLC, Portland, OR (US)

(72) Inventors: Patrick Edward Ferguson, Portland, OR (US); Patrick Joseph Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 379 days.

(21) Appl. No.: 14/285,791

(22) Filed: May 23, 2014

(65) Prior Publication Data

US 2015/0335327 A1    Nov. 26, 2015

(51) Int. Cl.

| A61B 17/06 | (2006.01) |
|---|---|
| D03D 1/00 | (2006.01) |
| D03D 3/00 | (2006.01) |
| A61B 17/82 | (2006.01) |
| A61B 17/84 | (2006.01) |

(52) U.S. Cl.
CPC ...... *A61B 17/06166* (2013.01); *A61B 17/826* (2013.01); *A61B 17/842* (2013.01); *D03D 1/00* (2013.01); *D03D 3/005* (2013.01)

(58) Field of Classification Search
CPC ............ A61B 17/06166; A61B 17/826; A61B 17/842; A61B 2017/06171; A61B 2017/0618; A61B 2017/06185; A61B 2017/0619; A61B 2017/06176; D03D 1/00; D03D 3/005

USPC ......................................................... 606/228
See application file for complete search history.

(56) References Cited

U.S. PATENT DOCUMENTS

| 4,979,956 A * | 12/1990 | Silvestrini .............. A61B 17/04 |
|---|---|---|
| | | 623/13.11 |
| 7,892,256 B2 | 2/2011 | Grafton et al. |
| 2005/0192631 A1 | 9/2005 | Grafton |
| 2009/0299407 A1 * | 12/2009 | Yuan ................ A61B 17/06166 |
| | | 606/228 |
| 2010/0274282 A1 | 10/2010 | Olson |
| 2010/0298872 A1 * | 11/2010 | Berndt ............. A61B 17/06166 |
| | | 606/228 |
| 2011/0054524 A1 | 3/2011 | Beevers et al. |
| 2012/0029561 A1 * | 2/2012 | Olson .............. A61B 17/06166 |
| | | 606/228 |
| 2012/0271416 A1 | 10/2012 | Mackay |

(Continued)

*Primary Examiner* — Katrina Stransky

(74) *Attorney, Agent, or Firm* — Timothy E. Siegel Patent Law, PLLC; Timothy E. Siegel

(57) ABSTRACT

A method of forming a suture tape assembly having a visually distinguishable midpoint includes weaving a longitudinally central portion of a length of round suture material together with other strands of material to form a length of suture tape. This suture tape has a longitudinal first end and a longitudinal second end, and the length of round suture material extends from both the first end and second end. Next, a center part of the length of the round suture material is grasped and pulled outwardly from the suture tape, to form a partial loop extending outwardly from the suture tape. This partial loop is cut from the suture tape, thereby leaving a longitudinally medial segment of the suture tape without the round suture material, and thereby being made visibly distinguishable from neighboring suture tape, which includes the round suture material.

14 Claims, 5 Drawing Sheets

(56) References Cited

U.S. PATENT DOCUMENTS

2013/0226233 A1  8/2013  D'Agostino et al.
2014/0364862 A1* 12/2014  Bennett ................ A61F 2/0811
                                                606/104

* cited by examiner

SUTURE TAPE ASSEMBLY HAVING A MIDPOINT MARK

BACKGROUND

The implantation of a suture during arthroscopic surgery may test the limits of the surgeon's skill. With a spotlight view of a section of a void inside the body, he cannot determine which section of a suture assembly he is viewing, adding to the challenge.

In a form of arthroscopic surgery for repairing a ball and socket joint, it is necessary to use suture tape to hold segments of bone together. To perform this task a suture assembly is provided that includes a longitudinal segment of suture tape with a round suture woven into the tape, but that is longer than the suture tape, extending out on either end, thereby forming a lead protruding from either side of the suture tape. The two leads are used to pull the suture tape into position, where it is attached to the bone with screws. Finally, the leads are cut off.

U.S. Pat. No. 7,892,296 describes an assembly of this type, and the surgery that can be performed using it. The suture assembly described, however, includes a round portion of high strength suture material that is woven into the suture tape. Unfortunately, high strength material is disclosed for the round suture that passes through the suture tape. Although it does not appear that high strength material is defined, there is generally a tradeoff between high strength and ease of handling. Also, because the round suture tends to protrude transversely from the tape, it may have a tendency to cut into bone. Moreover, because the leads, that is, the portion of the round suture material extending from the ends of the suture tape, are never called upon to bear a load, they do not require great strength. The choice of a high strength material, however, tends to reduce other desirable properties such as ease of handling. Also, there is not a way for a surgeon viewing the suture tape portion to be able to tell which part of that portion he is viewing.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a suture tape assembly that includes a first length of round suture and a second length of round suture and that is substantially aligned to the first length of round suture. Also, a tape section has a flattened profile and is provided as a flat braid formed of braided strands. This flat braid is formed around a portion of the first length of round suture and a portion of the second length of round suture, the flat braid being supported on the length of the round sutures and having a width greater than the thickness of either round suture. The lengths of the round sutures pass through a portion of the length of the flat braid, but are not present in a midpoint area of the flat braid. The tape section has a first end and an opposed second end, and the first length of round suture extends outwardly from the first end and the second length of round suture extends outwardly from the second end.

In a second separate aspect, the present invention may take the form of a method of forming a suture tape assembly having a visually distinguishable midpoint that includes weaving a longitudinally central portion of a length of round suture material together with other strands of material to form a length of suture tape. This suture tape has a longitudinal first end and a longitudinal second end, and the length of round suture material extends from both the first end and second end. Next, a center part of the length of round suture material is grasped and pulled outwardly from the suture tape, to form a partial loop extending outwardly from the suture tape. This partial loop is cut from the suture tape, thereby leaving a longitudinally medial segment of the suture tape without the round suture material, and thereby being made visibly distinguishable from neighboring suture tape, which includes the round suture material.

In a third separate aspect, the present invention may take the form of a suture tape assembly that has a length of round suture made of material that is not high strength material and a tape section that has a flattened profile and is provided as a flat braid formed of braided strands. This flat braid is formed around a portion of the length of round suture, is supported on part of the length of the round suture and has a width greater than the thickness of the round suture. The length of round suture passes through the length of the flat braid. Finally, the tape section has a first end and an opposed second end, and the length of round suture extends outwardly from the first end and the second end.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

A method for producing a suture tape assembly having a midpoint mark begins with work piece 10, that a length of round suture 12, which is preferably a US2 braid, typically formed of eight strands of polyester braided together to form a cover with three to six strands of polyester on the interior. In work piece 10, suture 12 has been braided as a central warp fiber into a length of flat suture tape 14, with the other warp fibers being made of twisted or braided ultra-high molecular weight polyethylene (UHMWPE). Suture 12 extends out of the two ends of suture tape 14, for about 12 inches. Suture tape 14 is between 3 and 4 feet in length.

Figure 1:
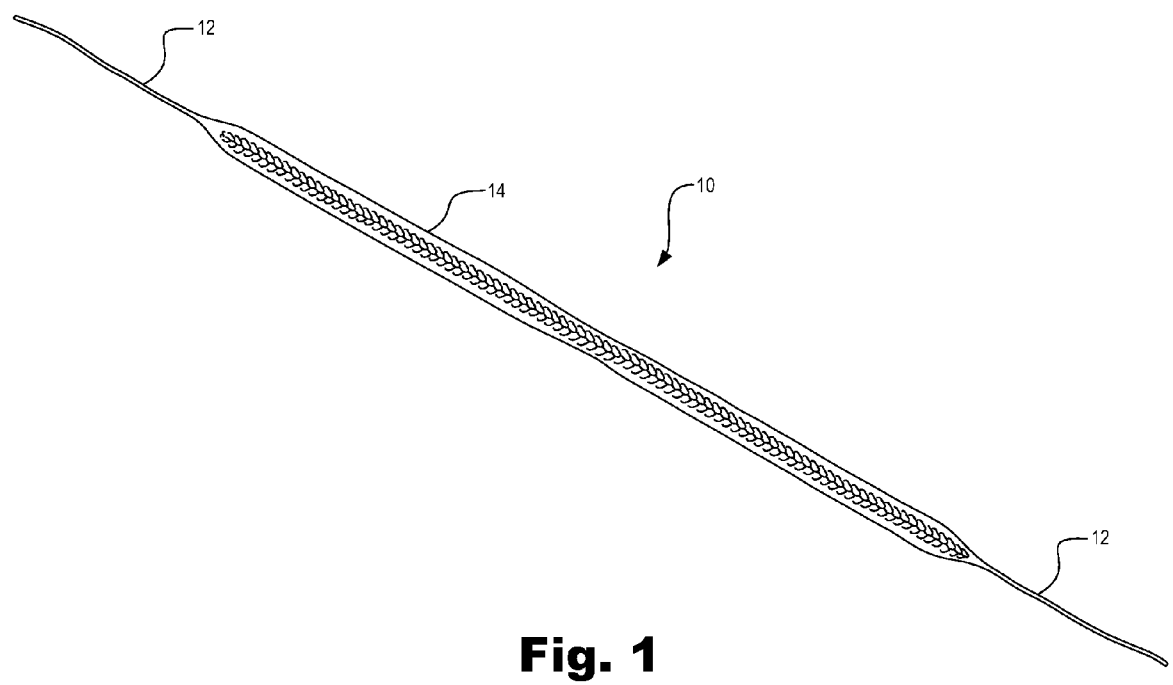
FIG. 1 is a plan view of a suture assembly work piece, used in the production of the suture assembly of the present invention.
Figure 2:
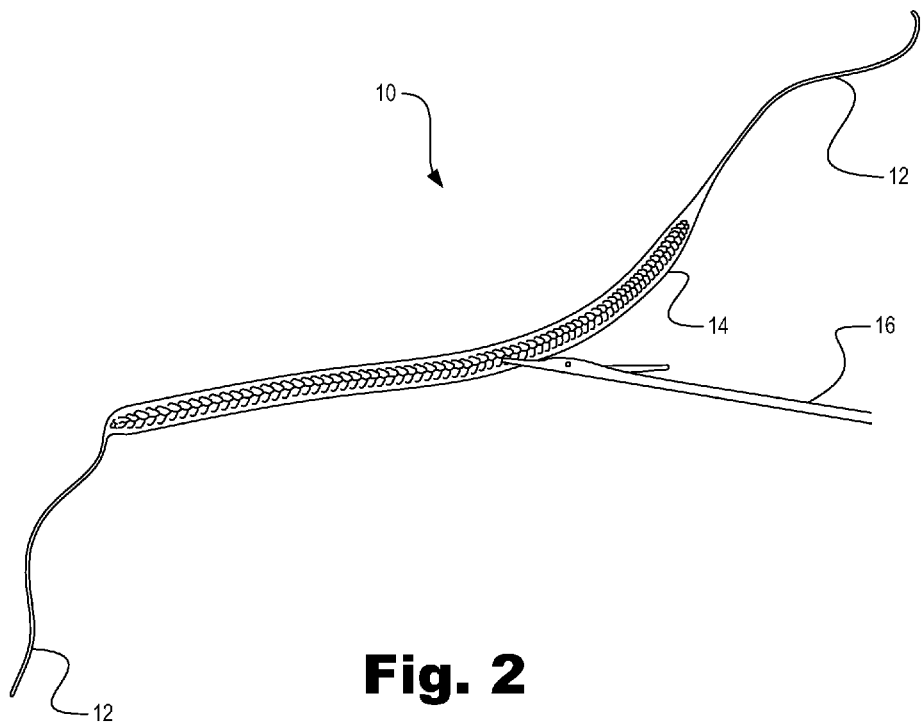
FIG. 2 is an isometric view of the suture assembly work piece of FIG. 1, being manipulated by a tool at a further stage in the production of a suture assembly.
Figure 3:
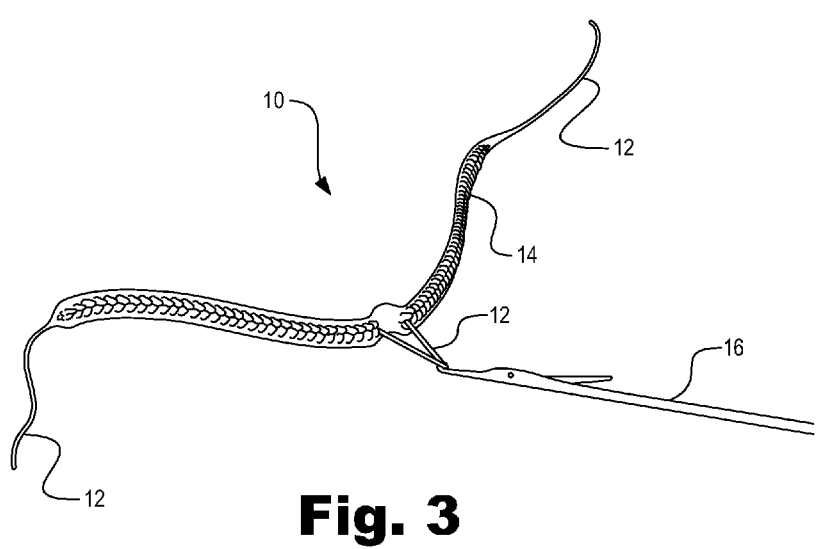
FIG. 3 is an isometric view of the suture assembly work piece of FIG. 1, being further manipulated by a tool, and shown at a still further stage in the production of a suture assembly.
Figure 4:
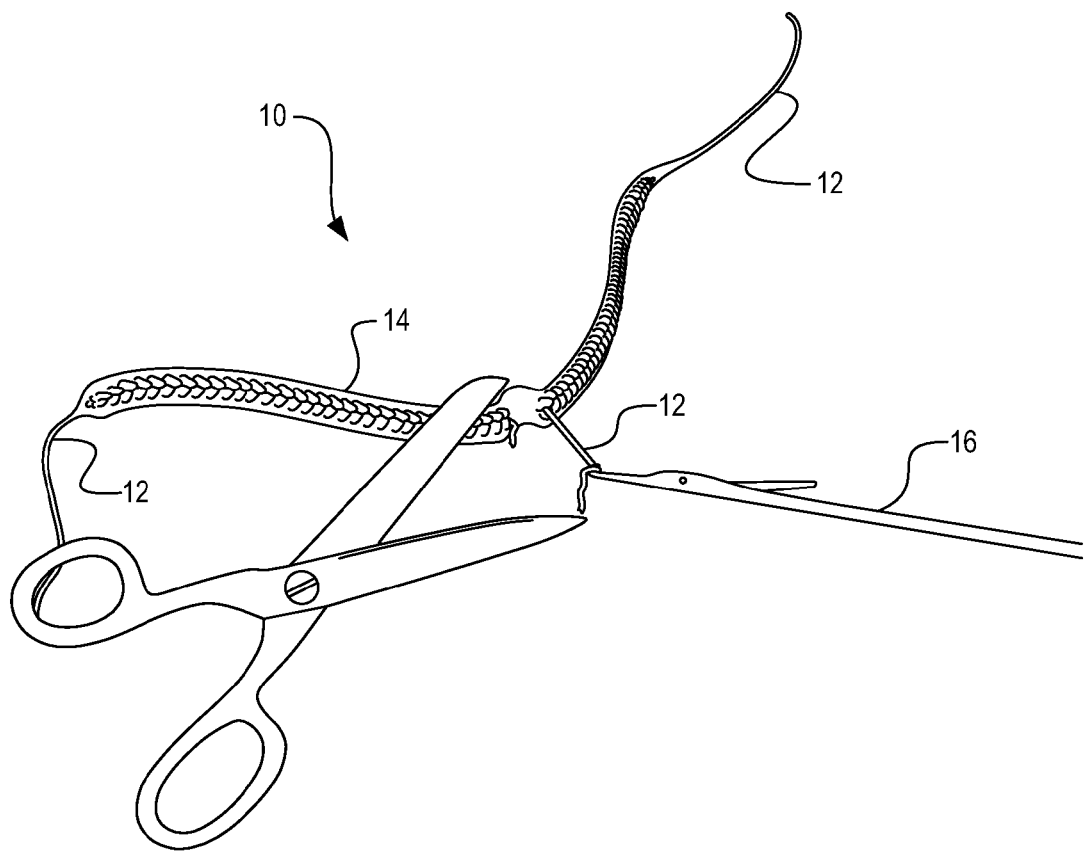
FIG. 4 is an isometric view of the suture assembly work piece of FIG. 1, being processed by two tools, and shown at a still further stage in the production of a suture assembly.
Figure 5:
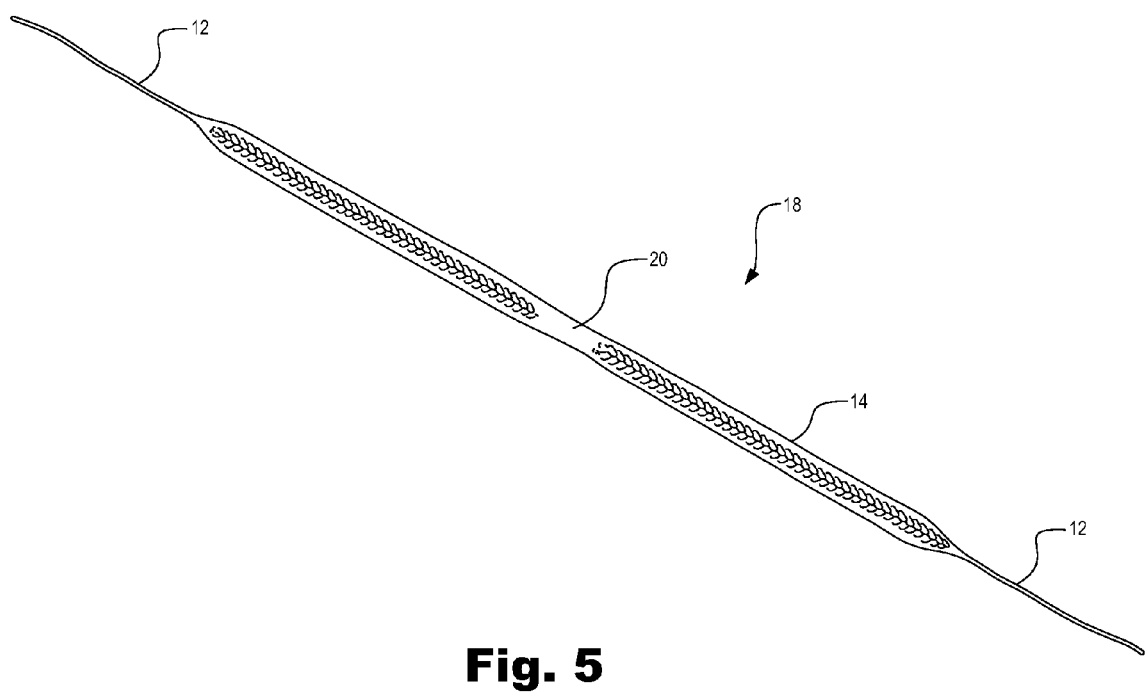
FIG. 5 is a plan view of a finished suture assembly, according to the present invention.

Referring to FIGS. 2 and 3, in the next step a lacing tool 16 is used to pull the suture 12 out from the midpoint of suture tape 14. About one to 5 inches of suture 12 are pulled out, creating a loop of suture 12, which is then snipped off (FIG. 4). Either end of suture 12 may then be pulled outwardly, so that the midpoint area of suture tape 14 has a different appearance from the rest of suture tape 14, and thereby completing suture tape assembly 18, which has a visually distinguishable midpoint 20 (FIG. 5).

During surgery, the surgeon may need to know which portion of the otherwise uniform-in-appearance suture tape 14 is being viewed. The midpoint reference mark 20 can guide him in this respect.

Figure 6:
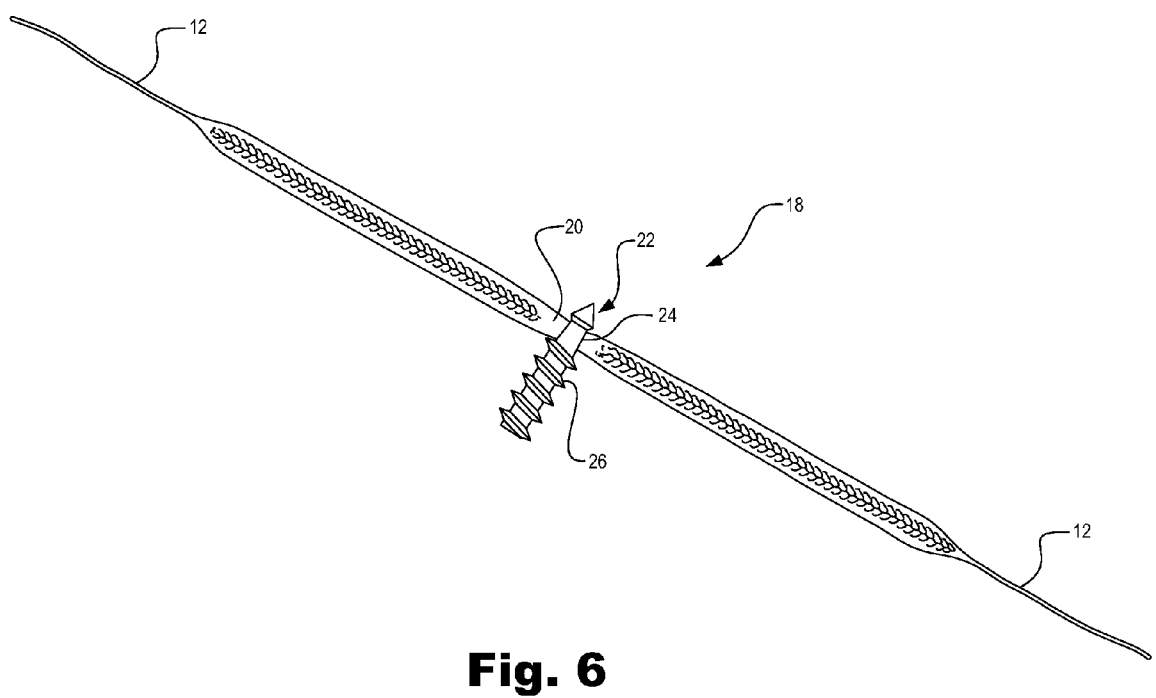
FIG. 6 is a perspective view of a finished suture assembly threaded into a bone anchor that has an aperture, according to the present invention.

Referring to FIG. 6, in order to use assembly 18, an anchor 22 that has an aperture 24 is threaded onto assembly 18. In this process, anchor 22 naturally settles into and stays at midpoint 20, which is thinner than the rest of assembly 18. As midpoint 20 is the spot where the anchor 22 is most advantageously placed, this greatly eases the task of the medical professionals performing a repair surgery with assembly 18.

In an alternative preferred embodiment, the operation of removing a portion of suture 12 is not performed, but a suture 12 that is not of high strength material is used. In the suture art, high strength is sometimes used to denote ultra-high molecular weight polyethylene. Other materials, such as polyester are softer, thereby reducing the chance of cutting into bone after implantation. Polyester also has superior handling qualities. As the tail ends of suture 12 are only used for placement of the tape portion 14 and are typically cut off after tape 12 is implanted, these tail ends do not have to be of high strength material.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A suture tape assembly, including:
   (a) a first length of suture and a second length of suture being substantially aligned to said first length of suture;
   (b) a tape section having a flattened profile and being provided as a flat braid formed of braided strands, said flat braid being formed around a portion of said first length of suture and a portion of said second length of suture, the flat braid being supported on said length of each said suture and having a width greater than the thickness of either suture, the lengths of said sutures passing through a portion of a length of said flat braid, but not being present in a midpoint area of said flat braid, said tape section having a first end and an opposed second end, and wherein said first length of suture extends outwardly from said first end and said second length of suture extends outwardly from said second end, said midpoint section of said flat braid being thinner than the rest of the tape section and visually recognizable by a surgeon performing a surgery; and
   (c) a bone anchor, defining an aperture and being engaged to said tape section by way of said tape section being threaded through said aperture and wherein said bone anchor naturally stays at said midpoint section, due to its relative thinness.

2. The suture tape assembly of claim 1, wherein said tape section is made of high molecular weight polyethylene, except for the portion formed from said first and second lengths of suture.

3. The suture tape assembly of claim 2, wherein said first and second lengths of suture are made of a material that is weaker than high molecular weight polyethylene and softer than high molecular weight polyethylene.

4. The suture tape assembly of claim 1, wherein said first and second lengths of suture are formed of polyester.

5. The suture tape assembly of claim 1, wherein said first and second lengths of suture are dyed.

6. The suture tape assembly of claim 5, wherein said first and second lengths of suture are dyed blue over a portion of their circumferences.

7. The suture tape assembly of claim 1, wherein said first and second lengths of suture are round in cross-section.

8. A method of forming a suture tape assembly having a visually distinguishable midpoint, comprising:
   (a) providing a length of suture material;
   (b) weaving a longitudinally central portion of said length of suture material together with other strands of material, to form a length of suture tape having a longitudinal first end and a longitudinal second end, and wherein said length of suture material extends longitudinally from both said first end and second end;
   (c) at a center of said length of suture tape, grasping said suture material and pulling a portion of it outwardly from said suture tape, to form a partial loop extending outwardly from said suture tape;
   (d) cutting said partial loop from said suture tape, thereby leaving a longitudinally medial segment of said suture tape without said suture material, and thereby being thinner than the rest of said suture tape and visually recognizable by a surgeon performing a surgery; and
   (e) providing a bone anchor that defines an aperture and threading said bone anchor onto said suture tape to said longitudinally medial segment, where said bone anchor naturally remains due to the relative thinness of said longitudinally medial segment.

9. The method of claim 8, wherein said other strands of material are made of high molecular weight polyethylene.

10. The method of claim 8, wherein said length of suture material is made of a material that is weaker than high molecular weight polyethylene and softer than high molecular weight polyethylene.

11. The method of claim 8, wherein said length of suture material is formed of polyester.

12. The method of claim 8, wherein said length of suture material is dyed.

13. The method of claim 12, wherein said length of suture material is dyed blue over a portion of its circumference.

14. The method of claim 8, wherein said length of suture material is round in cross section.

* * * * *